(12) United States Patent
Classen

(10) Patent No.: US 8,515,932 B2
(45) Date of Patent: *Aug. 20, 2013

(54) COMPUTER ALGORITHMS AND METHODS FOR PRODUCT SAFETY

(75) Inventor: John Barthelow Classen, Baltimore, MD (US)

(73) Assignee: Classen Immunotherapies, Inc., Baltimore, MD (US)

(*) Notice: Subject to any disclaimer, the term of this patent is extended or adjusted under 35 U.S.C. 154(b) by 249 days.

This patent is subject to a terminal disclaimer.

(21) Appl. No.: 13/156,916

(22) Filed: Jun. 9, 2011

(65) Prior Publication Data

US 2011/0238585 A1    Sep. 29, 2011

Related U.S. Application Data

(62) Division of application No. 10/081,705, filed on Feb. 21, 2002, now Pat. No. 7,984,069.

(60) Provisional application No. 60/270,697, filed on Feb. 22, 2001.

(51) Int. Cl.
*G06F 17/30* (2006.01)

(52) U.S. Cl.
USPC .......................... 707/705; 707/706; 707/710

(58) Field of Classification Search
USPC .......................... 707/705, 706, 710, 721, 790
See application file for complete search history.

(56) References Cited

U.S. PATENT DOCUMENTS

| | | | |
|---|---|---|---|
| 3,885,566 A | 5/1975 | Jacob | |
| 5,181,394 A | 1/1993 | Schea et al. | |
| 5,386,829 A | 2/1995 | Diamond | |
| 5,642,731 A | 7/1997 | Kehr | |
| 5,678,234 A | 10/1997 | Colombo et al. | |
| 5,723,283 A | 3/1998 | Classen | |
| 5,726,884 A | 3/1998 | Sturgeon et al. | |
| 5,728,385 A | 3/1998 | Classen | |

(Continued)

OTHER PUBLICATIONS

R. Evans et al., "Prevention of Adverse Drug Events through Computerized Surveillance", Proceedings of the Annual Symposium on Computer Application in Medical Care (1993).*

(Continued)

*Primary Examiner* — Hosain Alam
*Assistant Examiner* — Ahmed Abraham
(74) *Attorney, Agent, or Firm* — Browdy and Neimark, PLLC

(57) ABSTRACT

The invention comprises systems, methods and a computerized data management device for creating and using data relating to a medical or non-medical product or device to enhance the safety of the product or device. A vast amount of data regarding adverse events associated with a particular product or device is analyzed to identify new essential adverse events associated with the product or device. At least one database of new essential adverse event information is created and utilized, and new characteristics of or uses for the product or device related to the new essential adverse event information are determined. Adverse event information is gathered for a large number of population sub-groups. The system may also be programmed to incorporate the information into intellectual property and contract documents. Manufacturers and/or distributors can include the proprietary information in consumer safety information, which accompanies the product or device, or which is provided to patients, users, consumers and the like, or in the case of certain medical products or devices, to prescribers of those products or devices. The system and methods also provide for commercializing the essential adverse event information.

12 Claims, 6 Drawing Sheets

(56) References Cited

U.S. PATENT DOCUMENTS

| | | | |
|---|---|---|---|
| 5,737,539 A | 4/1998 | Edelson et al. | |
| 5,833,599 A | 11/1998 | Schrier et al. | |
| 5,845,255 A | 12/1998 | Mayaud | |
| 5,876,926 A | 3/1999 | Beecham | |
| 5,908,383 A | 6/1999 | Brynjestad | |
| 5,950,630 A | 9/1999 | Portwood et al. | |
| 5,970,463 A | 10/1999 | Cave et al. | |
| 5,991,751 A | 11/1999 | Rivette et al. | |
| 6,000,828 A | 12/1999 | Leet | |
| 6,018,714 A | 1/2000 | Risen et al. | |
| 6,097,995 A | 8/2000 | Tipton et al. | |
| 6,112,182 A | 8/2000 | Akers et al. | |
| 6,219,674 B1 | 4/2001 | Classen | |
| 6,221,851 B1 | 4/2001 | Feldman | |
| 6,243,615 B1 * | 6/2001 | Neway et al. | 700/108 |
| 6,323,242 B1 * | 11/2001 | Mueller | 514/646 |
| 6,458,958 B1 * | 10/2002 | D'Ambra et al. | 546/239 |
| 6,465,463 B1 * | 10/2002 | Cohn et al. | 514/248 |
| 6,584,472 B2 | 6/2003 | Classen | |
| 6,696,924 B1 * | 2/2004 | Socinski | 700/213 |
| 6,784,177 B2 | 8/2004 | Cohn et al. | |
| 6,944,776 B1 | 9/2005 | Lockhart et al. | |
| 2001/0001144 A1 | 5/2001 | Kapp | |
| 2002/0039990 A1 | 4/2002 | Stanton, Jr. | |
| 2002/0082930 A1 | 6/2002 | Park | |
| 2003/0004965 A1 | 1/2003 | Farmer et al. | |

OTHER PUBLICATIONS

U.S. Appl. No. 90/007,638, Jul. 22, 2005, Classen.
U.S. Appl. No. 90/007,639, Jul. 22, 2005, Classen.
Bradbury D. "A Bitter Pill to Swallow," Computing 34-35 (1995).
R.T. Chen, et al., "vaccines Safety Datalink Project: A New Tool for Improving Vaccine Safety Monitoring in the United States," Pediatrics. 99:(6) 765-773 (1997).
DeStefano, et al., "Timing of Hepatitis B Vaccination and Risk of Insulin-Dependent Diabetics Mellites", Pharma. and Drug Safety 6(2) (1997).
*Baker v. Secy of Dept. of Health and Human Services*, No. 99-653V, 2003 WL 22416622, (Ct. Fed. C. Sep. 26, 2003).
A. Bate, et al., "A Bayesian neural network method for adverse drug reaction signal generation," Eur. J. Clin. Pharmacol. 54 (4) (Jun. 1998) 315-321.
C. Baum, et al., "The Spontaneous Reporting System in the United States", Pharmacoepidemiology, 2nd ed. New York: John Wiley Son & Sons, 1994, 125-137.
D. Classen et al., "Adverse Drug Events in Hospitalized Patients", 277 JAMA, 301-306 (1997).
D. Classen et al., "Decription of Computerized Adverse Drug Events in Hospital Patients", 266 JAMA, 2847-2851 (1991).
D. Classen et al., "Description of a Computerized Adverse Drug Event Monitor Using a Hospital Information System", 27 Hosp. Pharm. 774, 776-779, 783 (1992).
D. Classen & S. Pastotnik, "The Computer-Based Patient Record", Hospital Epidemiology and Infection Control, 141-154 (2nd Ed., New York: Lippincott Williams & Williams 1999).
R. Evans et al., "A Computer-Assisted Management Program for Antibiotics and Other Antiinfective Agents", 338 The New England Journal of Medicine, 232-238 (1998).
R. Evans et al., "Development of Computerized Adverse Drug Event Monitor", 15th Annual Symposium on Computer Applications in Medical Care, 23-27 (1992).
R. Evans et al., "Evaluation of a Computer-Assisted Antibiotic-Dose Monitor", 33, Annals. Pharm., 1026-1031 (1999).
R. Evans et al., "Preventing Adverse Drug Events in Hospitalized Patients",28 Ann. Pharm. 523-527 (1994).
R. Evans et al., "Prevention of Adverse Drug Events through Computerized Surveillance", 16th Annual Symposium of Computer Applications in Medical Care, 437-441 (1993).
R. Evans et al., "Using a Hospital Information System to Assess the Effects of Adverse Drug Events," Seventeenth Annual Symposium on Computer Applications in Medical Care, 161-165 (1994).
G. Faich, U.S. Adverse Drug Reaction Surveillance 1989-1994, Pharmacoepidemiology and Drug Safety 5:393-398 (1996).
Federal Register, vol. 58, No. 105, (Jun. 3, 1993).
Finney, D. J., Systematic Signaling of Adverse Reactions to Drugs, Methods of Information in Medicine, 13 (1974) 1-10.
International Reporting of Adverse Drug Reactions, Final Report of CIOMS Working Group, 1990.
Jim Kling, "From Hypertension to Angina to Viagra", Modern Drug Discovery 1(2) (1998), available at http:pubs.acs.org/hortartc/mdd/98/novdec/viagra.htm.
M. Linguist et al., "From Association to Alert-A Revised Approach to International Signal Analysis", Pharmacoepidemiology and Drug Safety 8:S15-S25 (Apr. 1999).
David J. Morrow, "New Profits in Old Bottles", N.Y. Times, Mar. 19, 1999.
C. A. Naranjo et al., "A method for Estimating the Probability of Adverse Drug Reactions", 30 Clin. Pharmacol. Ther. (2):239-45 (1981).
V. Pinkston & E.J. Swain, "Management of Adverse Drug Reaction and Adverse Event Data through Collection , Storage and Retrieval", Detection of New Adverse Drug Reactions, 281-296 (Apr. 1998) (4th Ed., London: Macmillan Reference Ltd.).
"Post-marketing surveillance for adverse events after vaccination: the national Vaccine Adverse Event Reporting System (VAERS)," MEDWATCH Continuing Education Article (1998).
Statement of Susan S. Ellenberg before the U,S, House of Representatives, available at www.fda.gov/ola/1999/anthrax.html.
A. Szarfman, "Discussions: A Report on the Activities of the Adverse Events working Groups: Focus on Improving the Detection of Rare but Serious Events," 1999 Proceedings of the Biopharmaceutical Section, American Statistical Association, Alexandira (VA), American Statistical Association, 12-13 (1999) (Szarfman/abstract).
A. Szarfman, "New Methods for Signal Detection", 15th International Conference on Pharmacoepidemiology, Boston, Mass., Aug. 28, 1999 (Szarfman/ppt).
U.S. Food and Drug Administration, "What is a Serious Adverse Event?", http://www.fda.gov/medwatch/report/DESK/advevnt.htm.
Vaccine Safety Forum, Summaries of Two Workshops, Washington, D.C. (National Academy Press 1997).

\* cited by examiner

COMPUTER ALGORITHMS AND METHODS FOR PRODUCT SAFETY

REFERENCE TO RELATED APPLICATIONS

This application is a divisional application of U.S. application Ser. No. 10/081,705, filed Feb. 21, 2002, the entire contents of which is hereby incorporated by reference, and claims the benefit of U.S. Provisional Application No. 60/270,697, filed Feb. 22, 2001, which filing date is claimed herein, and the content of which is herein incorporated by reference.

FIELD OF THE INVENTION

The present invention involves the fields of products, including drugs, medicaments, biologicals, devices, food additives, chemicals and other products or devices, that may have essential adverse events, as well as computer databases for generating, storing, analyzing and processing information related thereto.

BACKGROUND OF THE INVENTION

Computers, systems and methods for screening databases to determine new adverse events and to develop proprietary new uses and proprietary kits containing warnings pertaining to the new adverse event information have been described in U.S. Pat. No. 6,219,674 and U.S. patent application Ser. No. 09/804,289. However, the systems and methods described in the '674 patent were less than ideal because not all adverse event information is commercially valuable. In order for adverse event information to be valuable it must be patentable (i.e. proprietary) by being novel, non obvious and having utility. Likewise, the systems and methods described in the '289 patent were less than ideal because, even if the adverse event data is patentable, it is not commercially valuable unless it is essential, that is, the information must be such that all manufacturers would need to include it with the sale of the corresponding product. Otherwise, manufacturers would continue to sell their products without the subject information. Conversely, if one were to simply patent all new uses for the product, drug, and the like, considerable time and money would be consumed, but there would by a low probability for commercial or financial return on the whole.

The government has carefully established codes and rules under which, for example in the medical field, manufacturers and/or distributors are required to notify or warn the public of known adverse events which could occur when certain products, including drugs, medicaments and the like, are ingested or used by human or veterinary patients. Regulations also apply to chemical products, including food supplements, which may be absorbed, ingested or inhaled. Similar notice or warnings must be attached to devices, particularly to medical devices. Moreover, if the warnings are not present, the product or device not only must be immediately removed from use by, and availability to, the public, but also significant fines and penalties can be levied against the manufacturer and/or distributor of the product or device for its failure to provide adequate notice and warning to the public. In addition, because such manufacture and/or distribution was permitted without the required notice or warning, the manufacture and/or distribution was practiced in violation of the law. As a result, those manufacturers and/or distributors risk criminal and/or civil liability to anyone adversely affected by the product or device during the time when it was on the market.

The government has failed to establish mechanisms by which products and devices are adequately screened for safety, i.e., for the possibility of essential adverse events which could affect the safety of the patient using the product or device. This is particularly true for medical products and devices. The screening that is conducted by manufacturers and/or distributors of such products and devices is typically small in scale and incomplete for all possible adverse events. Consequently, until the present invention, there has been a need in the art for reliable screening methods to eliminate or minimize the possibility of an essential adverse event that could affect a patient or consumer using a product or device, so that the consumer can trust that the product or device is "safe."

In addition, the prior art has failed to contemplate business methods which involve detecting essential adverse events relating to a product or device, and then offering the refined proprietary data from such screens to the manufacturers and/or distributors of the product or device. Once the existence of such essential adverse data is known to the manufacturer and/or distributor, they are obligated to inform the public of the potential adverse event, or they must remove the product or device from the market. Because manufacturers are currently producing and distributing products and devices without restrictions on their use, they are available for use in screens to develop essential adverse event data, which when refined, would become proprietary. Thus, there also exists a substantial market for such refined, proprietary, essential adverse event data, and for the methods, systems and devices by which it is obtained, which would (1) meet the need in the art for steps which would enhance public safety with regard to the use of products and devices, and (2) offer to manufacturers and/or distributors of product and/or devices a way to (a) significantly improve public safety, (b) permit their products and devices to remain on the market, and (c) reduce their risk of liability for the occurrence of an adverse event with the use of their products or devices.

SUMMARY OF THE INVENTION

The current invention permits not only ways of screening for new, previously unrecognized adverse events associated with the use of a product or device, but also a method, system and device for determining which new adverse events and new uses are "essential." The method, system and device permit a technician or computerized system to detect new essential adverse events and identify new useful characteristics or uses for a product or device, and commercialize the essential adverse data information.

In some instances a manufacture or distributor is given the option of adding notifications or warnings that a product or device is associated with an essential adverse event, or they can perform safety studies to show the product is safe in light of the newly recognized, essential adverse event (essential methods of screening a product for safety). Thus, the invention relates to data processing methods and system for developing product safety information to be included in the package information which would accompany a commercial product or device. The current methods and system further provide for the detection and development of methods of screening a product or device for consumer safety.

In preferred embodiments, the data processing system comprises: at least one adverse event database for storing adverse event data associated with a product or device; a processor for accessing and analyzing the data to assist in identifying new essential adverse events associated with the product or device and to assist in identifying at least one new useful characteristic of, or use for, the product or device responsive to identification of at least one new essential adverse event associated with the product or device; an adverse event information storage device for storing the new essential adverse event data identified by the processor; a computer for requesting and receiving adverse event information from the processor; and a user interface for interfacing with the processor and the computer.

The present invention is further embodied by a method for creating and using data associated with a product or device comprising: accessing at least one adverse event data source that stores adverse event data associated with a product or device; analyzing the adverse event data to identify new essential adverse events associated with the product or device; analyzing data from the data source to identify at least one new useful characteristic or use for the product or device responsive to identification of at least one new essential adverse event; creating at least one essential adverse event information database, wherein the adverse event information includes at least one new characteristic or use; and commercializing essential adverse event data stored in the essential adverse event information database.

The invention is also embodied by a method of establishing at least one new use for a product or device comprising: comparing adverse event data associated with a product or device with previously known adverse event data associated with the product or device; observing at least one new adverse event associated with the product or device; determining whether the new adverse event associated with the product or device is an essential adverse event; and identifying at least one new useful characteristic of, or use for, the product or device responsive to the determination that the at least one new adverse event associated with the product or device is an new essential adverse event.

In addition, the invention is embodied by a computer for managing product or device related data comprising: at least one adverse event database storing adverse event data associated with a product or device; a processor for accessing and analyzing the data to assist in identifying new essential adverse events associated with the product or device and to assist in identifying at least one new useful characteristic of, or use for, the product or device responsive to identification of at least one new essential adverse event associated with the product or device; and an essential adverse event information storage device for storing essential adverse event data including the at least one new essential adverse event associated with the product or device, and the at least one new characteristic of, or use for, the product or device identified by the processor.

Moreover, the method and system further provide for commercializing the essential adverse event information.

Further, the invention is embodied by methods and systems by which the detected information is formatted and compiled into contract documents, which are then used in licensing the essential adverse event information to manufacturers and/or distributors, who can then include the essential adverse event information in their product information, which is provided to consumers or prescribers of the product or device. Moreover, such contract documents can be used to license the essential adverse event information to potential competitors of the manufacturer and/or distributor.

The embodied invention also provides marketing and packaging methods, in which the use of the subject product or device is restricted by a licensing agreement or contract, which would exclude using the product or device for the detection and patenting of essential new adverse event information.

The invention also pertains to any product or device created using the essential adverse event data of the method, system or device of the present invention; as well as uses therefore.

The invention also provides a kit containing the product or device, and labeling notifying the user of at least one new essential adverse event for the product or device. Additionally provided are methods comprising using the kit in accordance with a new characteristic of, or use for, the product or device.

The invention is especially useful in detecting and preventing essential adverse events related to, or caused by, medical products including drugs, medicaments and biologicals, and medical devices.

Other objects, features and advantages of the present invention will be clear to those skilled in one or more of the relevant arts, based on the teachings and guidance presented herein.

DESCRIPTION OF THE DRAWINGS

The foregoing summary, as well as the following detailed description of the invention, will be better understood when read in conjunction with the appended drawings. For the purpose of illustrating the invention, there are shown in the drawings, certain embodiment(s) which are presently preferred. It should be understood, however, that the invention is not limited to the precise arrangements and instrumentalities shown.

DETAILED DESCRIPTION OF THE INVENTION

The inventor's prior invention, U.S. Ser. No. 09/449,178 (now allowed) describes a computer system and method for deriving new uses based on new adverse events, which also finds application in the present invention. However, the currently embodied system and method of the invention provides for the further purification or refinement of adverse event information to develop new proprietary uses for a product, such as a drug, or for a device. The system and methods provide detecting "essential" adverse event information or "essential" new uses based on the adverse events or "essential" new methods of screening a product for safety.

Figure 1:
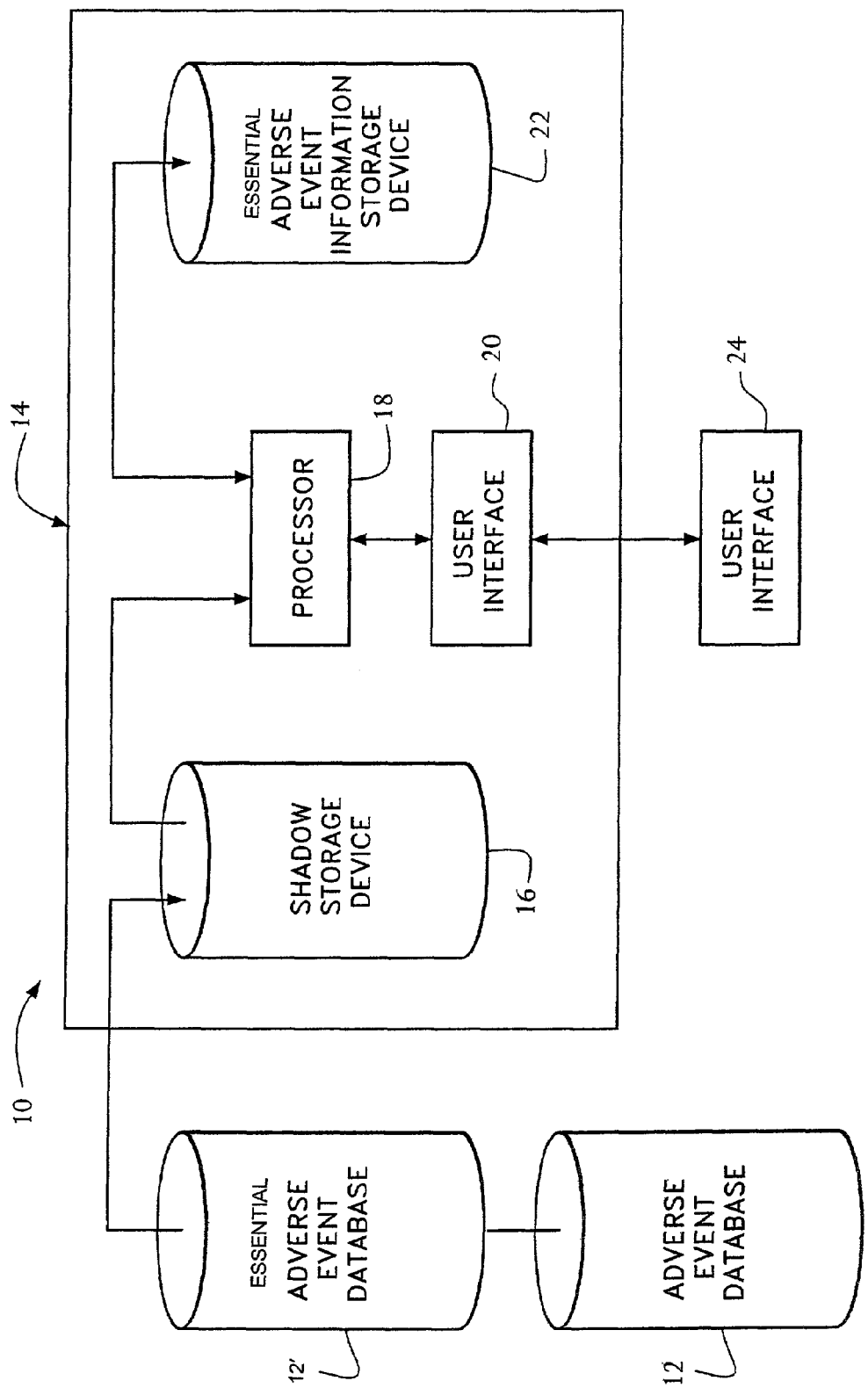
FIG. 1 is a schematic view of a first embodiment of a system according to the present invention.

Referring to the drawings wherein like references indicate like elements throughout the several views, there is shown in FIG. 1 a first system 10 constructed in accordance with the present invention. System 10 includes at least one adverse event database 12, at least one essential adverse event database 12' and a server 14. Depending upon the source, the adverse event database(s) 12 may be accessed by server 14 free of charge or for a fee. Essential adverse event database 12', preferably contains large amounts of data regarding a particular "essential" medical or non-medical product or device.

The term "medical" as used herein shall be construed to mean drugs, vaccines, non-vaccine biologicals, medical devices and any other medically-related goods and therapies.

Drugs and biologicals as the terms are herein used within the term "medical product," are intended to encompass any known, or as yet unknown, class of drug, medication or biological therapeutic (including inhibitors, preventors, enhancers activators, stimulants, catalysts, promoters, regulators, and the like). These can be categorized by their effects on an organ system, such as cardiac, respiratory, renal etc. Drugs and biologicals are also classified by their chemical composition, e.g., sulfa drugs, penicillin derivatives, vaccines, immune stimulants, antibiotics, etc. In addition, they can be classified according to their activity, e.g., diuretic, antibiotic, beta-blocker, etc.

Medical devices can be similarly classified by those of ordinary skill in the art, e.g., medical devices may be grouped as defibrillators, EKG machines, infusion pumps, CT machines, etc. To further assist in the categorization process, those skilled in the art may consult medical science resources such as medical libraries or online authorities such as MEDLINE® and the like to locate articles, books or other printed or electronic publications on the subject of interest such as the non-limiting example of Goodman and Gilman's "The Pharmacological Basis of Therapeutics."

"Non-medical product or device" shall be construed to mean any non-medically-related product or device that may cause harm to a consumer including, without limitation, foods, food additives, beverages, vitamins, alcohol, tobacco, cosmetics, mechanical devices and children's toys, personal and household cleaning products, and other chemicals such as paints and related coatings, insecticides, herbicides and industrial chemicals.

Because of the large volume of data that they contain, preferred adverse event databases may include those of insurance companies, managed care organizations, pharmaceutical and medical device manufacturers and/or distributors, public health departments, hospitals and the like. Typically, each adverse event recorded in such databases links the adverse event with demographic information such as but not limited to, the age, sex and race and, frequently, one or more physical condition factors of the individual that experienced the essential adverse event. The result is that adverse event database 12 may contain thousands or even millions of items of data. Such vast repositories of information enable the data to be analyzed to generate statistically relevant and reliable information relating to age, gender, racial, physical condition or other subgroup. The essential adverse event database 12' is a refinement of the adverse event data procured from the adverse event database 12, based upon selection of adverse data that is "essential" as defined below.

Server 14 preferably includes a shadow storage device 16, a processor 18, a user interface 20 and an essential adverse event information storage device 22. Shadow storage device 16 gathers and stores essential adverse event data received from the adverse event database(s) 12. Processor 18 comprises any computer processing means suitable for executing the operations of the present method as described hereinafter. User interface 20 includes any suitable input/output (I/O) equipment. Essential adverse event information storage device 22 stores adverse event information that is generated by processor 18 responsive to analysis of the essential adverse event data stored in shadow storage device 16. The shadow and essential adverse event information storage devices 16, 22 may be any memory devices capable of storing large amounts of information. Lastly, system 10 includes a user computer 24 for interfacing with user interface 20. User computer 24 is preferably any commercially available personal computer, workstation or the like which can exchange information with user interface 20 in the manner well known in the art.

If the event data relating to a product or device is both essential and desired, the essential adverse event data in adverse event database 12' can be collected using the ICD and other disease codes on admission, discharge, pharmaceutical sales, physician visit records or other known sources. The system of the present invention also accommodates and processes animal safety test data such as animal toxicity data.

Through operation of system 10 and the other systems described herein, the data extracted from the adverse event database 12 is analyzed by suitable programming of processor 18 to produce useful essential adverse event information that collected into essential adverse event database 12' and is storable in essential adverse event information storage device 22. For example, the adverse event database stores information on frequency of essential adverse events, such as but not limited to, death, illness, hospitalization, office visits, disability, missed work, medical costs, abnormal lab results and surgeries in individuals receiving the product or device in question, and this information can be compared to the observed adverse event rate in the same persons before receiving the medical product or in persons of similar characteristics (i.e., a control group). The analysis is performed on different exposure rates including, but not limited to the amount, duration and timing of exposure to the product or device.

The "adverse events" refer to, for example, damage or alteration to any organ system, including the non limiting examples of cardiac, respiratory, gastrointestinal, endocrine, muscular, skeletal, liver, renal, spleen, neurological, skin, blood, immune, and bone marrow. These adverse events further include the development of new diseases, including the non limiting examples of seizures, cancers, heart disease, arrhythmia, autoimmune disease, and allergy. Moreover, failure of a person to respond beneficially to a drug can be considered an adverse event. Preferably, the adverse event (or new use) is one other than one related to dosing including the timing of dosing (or optimizing dosing).

The database to be screened for new adverse events comprises adverse event information relating to the use of products in or devices on humans or animals. While human data is more valuable for determining new uses in humans, it is possible that new adverse events detected in animals can be used to develop new product characteristics or uses in humans. An example is detection of birth defects, or drug interactions in animals, which preferably leads to new uses comprising restricted use in pregnant humans or humans taking certain drugs.

Databases of adverse event information can be created by screening animal models of specific human diseases and cell culture models of human diseases for the potential new adverse events. In this situation an animal model of human disease is exposed to the product and the frequency or severity of the disease is recorded compared to a control group. Ideally the product is exposed to as many different animal models of human diseases as possible or feasible.

In a similar manner a culture of cells can be exposed to a product in many instances. This is easily accomplished if the product is a drug, chemical, or emits radiation. The cells may be normal cells, premalignant or malignant cells. One can compare the outcome of product on the cells to that of the effect on control cells. Endpoints include the non limiting examples of cell death, cell mutation and cell division. Ideally the product or device is exposed to as many different animal models of human diseases as possible or economically feasible.

One can use the data from the database to compare to previously known adverse events to determine new adverse event information. The order by which one checks for an adverse event can vary, and any order that is suitable is acceptable. For example, one can hypothesize that a product causes one or more adverse events. One can then analyze the data to see if the product causes an adverse event, and then determine if the adverse event is new. Alternatively, one can hypothesize that a product causes an adverse event and then check databases to see if it has been reported that the product is associated with an adverse event. If the association has not been reported than one can screen raw adverse event data/databases to see if the product is associated with the adverse event. If data does not exist to test the hypothesis using available raw adverse event data, then new data can be generated in the form of a study. In most cases, this would involve animal toxicity studies since performing prospective studies in humans to prove adverse events is generally unethical.

By "raw data," as used herein, means data before it is processed and analyzed. For example, the raw efficacy or adverse event data relating to a drug would include all of the collected data, which is linked to individuals who used the drug, or in some instances for a product such as tobacco, for those exposed to the product. This raw data comprises, e.g., the individual's weight, height, race, lab results, medical conditions and length of use or exposure to a product or device. By contrast, "processed data" means analyzed data that has been categorized or qualified to meet the requirements or standards of a particular situation.

In a preferred embodiment, one searches existing adverse event databases for adverse events, then determines if associations discovered are new. An additional study can be performed to verify the finding. In another preferred embodiment, one can hypothesize about certain adverse events, and then determine if they have been reported. If they have not, then raw adverse event data would be analyzed to determine if there is an association.

Additional adverse event information may also be derived from subgroup analysis. Subgroup analysis is performed to determine specific high risk groups who may be at increased risk of having an essential adverse event. Subgroups include persons with similar characteristics, such as but not limited to, sex, age, race, weight, height, percent body fat, genetic characteristics, pregnancy status, allergies, additional medical problems, use of additional medical products (including devices), past medical history, family history, social history, occupation, use of alcohol, tobacco, recreational drugs, and history of abnormal lab tests such as EKG, chest x-ray, liver function test and kidney function test. Similarly, subgroups are intended to include without limitation high risk associated groups such as high or low temperatures, chemicals, surfaces, pressures, electricity and sparks; or contact of the product or device with one of the group consisting of skin, eyes, ears, respiratory surfaces, gastrointestinal surfaces and mucous membranes of the consumer, or to a subpopulation group selected from the group consisting of children, pregnant women, consumers with specific allergies or medical conditions and animals. Preferably this demographic data, i.e., sub group information, is available through history and physical, where no additional laboratory test is needed for a new use. The subgroup analysis can include groups that were not represented or were under-represented in safety studies that were required for marketing approval or were done around the time of market introduction. For example, a drug may be approved for use in persons over the age of 18. However, people under 18 may also receive the drug. In such case, packaging for the drug may not include sufficient warnings for persons under 18, in general, and subgroups of persons under 18, in particular, that are at greater risk of essential adverse events linked to usage of the product or device.

Studies, as described above and in other sections of this document, however do not prove a product or device causes an adverse event, only that the adverse event and the product or device are associated. In some instances there may be a direct link. For example, wealth or standard of living is associated with certain adverse events. Money does not cause the adverse events, but it allows wealthy individuals to buy products that cause a specific adverse event. If an epidemiology study does show an association between an adverse event and a product or device, then there is a risk that the associated product or device caused the adverse event.

This risk exists even if the association is not statistically significant. However the risk is greater if a statistically significant association exists. Since some of the associations are true causal relations, knowledge that a risk exists has utility since one can avoid the risk when one knows it exists.

Ideally, systems according to the invention track large numbers of variables to locate groups at high risk of essential adverse events. As a non-limiting example, the systems are configured to track people taking multiple different drugs to determine whether a toxic adverse event occurs in people taking all of the drugs at once. The systems utilize statistical formulae to identify groups at high or low risk of essential adverse events. Preferably the database of adverse events associated with a product contains multiple different adverse events and is not limited to a single type, such as diabetes, birth defects, or the like.

The systems according to the invention also optionally collect and analyze efficacy data. The benefit of the product or device in certain subgroups can thus be measured by observing the frequency of the intended benefit (e.g., decreased death, stroke, kidney failure, and so on). Benefits also include reductions in costs where the costs may include, without limitation, costs of the product or device, expenses and lost productivity. By using the data from the risks and benefits, one can determine the risk/benefit for persons in any particular subgroup.

This information can be highly stratified to enable, in addition to previously known uses, new, different or more precise uses for a product or device. For example, a dose of a drug or biologic, the frequency or manner of use of a device, or the setting of a device such as a pacemaker may be precisely prescribed to accommodate the individual needs of particular subgroups.

Targeted searches can be performed and their data analyzed by the systems of the present invention. For example, if it is discovered from one adverse event database 12 that persons receiving a medical product are at increased risk of dying of liver failure at a certain dose of medication or when taking the drug in combination with other drugs, then one can verify the findings using a second adverse event database 12. Adverse event data from either adverse event database can also be confirmed in animals or by prospective clinical trials in humans. Targeted searches can also be done after case reports of adverse reactions, discovery of adverse events in animals, adverse events discovered in similar products and possible adverse found in small studies.

Consistent with the invention, any number or variety of proprietary databases are storable on essential adverse event information storage device 22. For instance, a first proprietary database created containing information about a particular product's or device's adverse events and, optionally, risk benefits and cost benefits of the product or device. The data from that database is crossed, linked or compared with a database of knowledge already accumulated on the product or device that may also be stored on essential adverse event information storage device 22. Sources of prior known essential adverse events can include package inserts, the Physician's Desk Reference, The Merck Manual, data from regulatory agencies such as the FDA, and published literature found on databases such as MEDLINE®. In the future it is contemplated that databases of patents and patent applications will also contain known adverse events. Likewise, the databases can comprise commercial or sales data. New findings on essential adverse reactions can thus be determined through appropriate comparison and/or interpretation of the databases.

The newly derived knowledge can include, without limitation, catalogs of new adverse events, specific frequency of adverse events, drug interactions and side effects in specific subgroups such as those mentioned above. For instance, a new essential adverse event can mean a newly discovered adverse reaction such as the discovery of an increased rate of seizures associated with a drug, improved information such as more accurate calculation of the rates of seizures in a group or subgroup, or the discovery of an increased rate of seizures in patients taking the drug along with one or more additional drugs.

Figure 2:
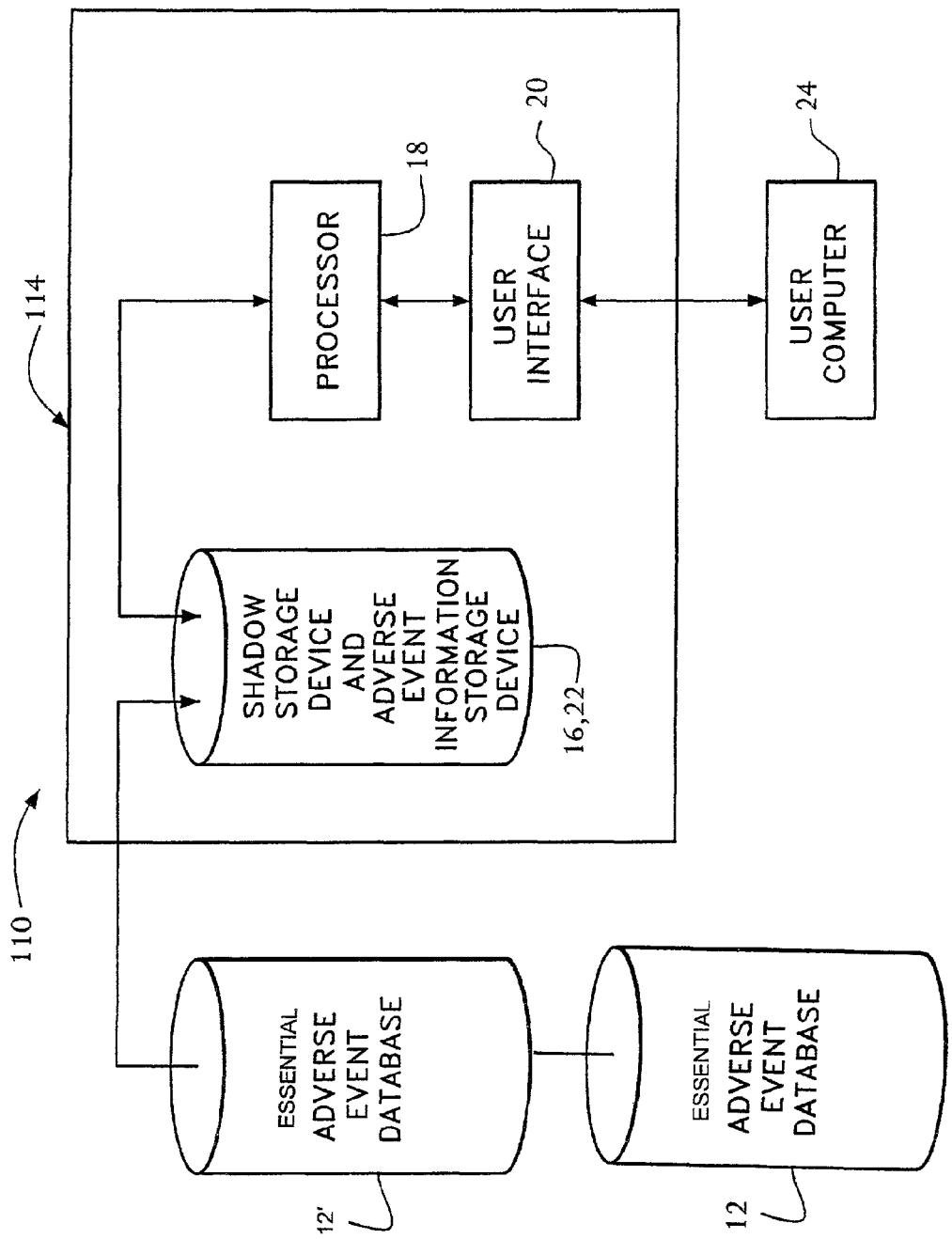
FIG. 2 is a schematic view of a further embodiment of a system according to the present invention.

FIG. 2 represents a further preferred embodiment of a system according to the invention identified by reference numeral 110. System 110 is constructed and functions substantially similarly to system 10 of FIG. 1 with the exception being that the shadow storage device 16 and essential adverse event information storage device 22 of system 10 are integrated into a single shadow storage device and essential adverse event information storage device 16, 22 on server 114.

Figure 3:
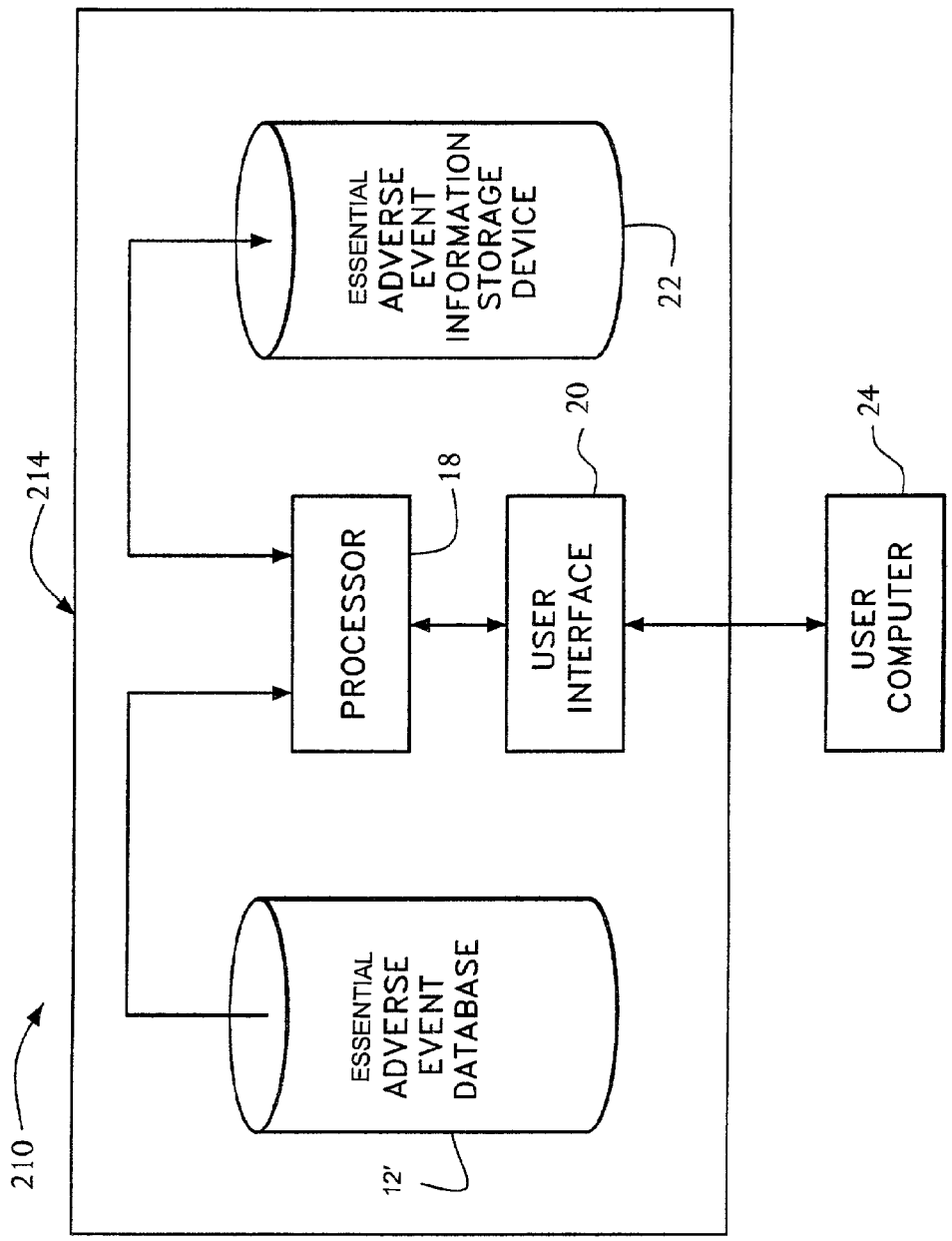
FIG. 3 is a schematic view of a further embodiment of a system according to the present invention.

FIG. 3 represents a further preferred embodiment of a system according to the invention identified by reference numeral 210. System 110 also is constructed and functions substantially similarly to system 10 of FIG. 1. However, unlike systems 10 and 110, system 210 draws its essential adverse event data from an internal rather than an external source; that is, server 214 of system 210 directly supports essential adverse event database(s) 12'. System 210 graphically depicts a situation wherein a holder of a substantial body of adverse event data itself analyzes such data using processor 18 and creates one or more adverse event information databases that are stored on essential adverse event information storage device 22.

Exemplary users of system 210 may include, for example, insurance companies, managed care organizations, pharmaceutical and medical device manufacturers and/or distributors, public health departments, hospitals and the like. Although illustrated as separated devices, it is also contemplated that essential adverse event database(s) 12' and essential adverse event information storage device 22 may be integrated into a single storage device.

Figure 4:
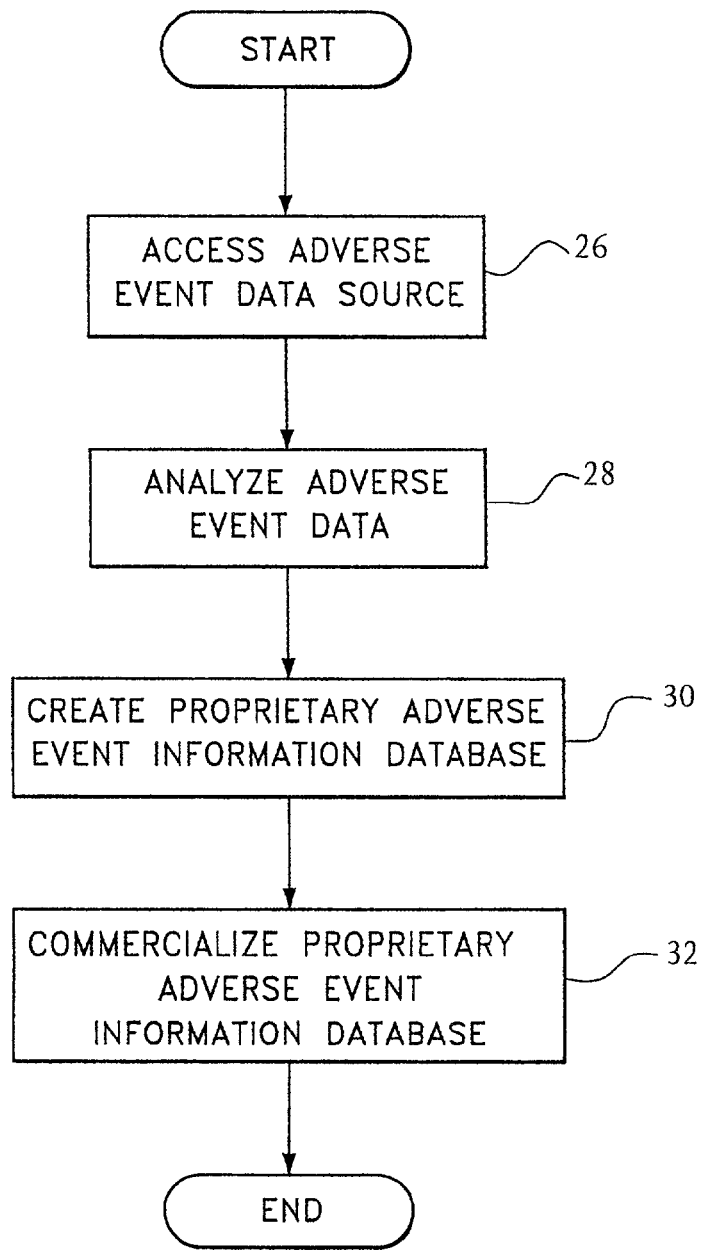
FIG. 4 is a flow chart illustrating the method according to the present invention.

FIG. 4 is a flow-chart that embodies the essential method steps of the present invention that are executed by each of systems 10, 110 and 210. At step 26, the adverse event database(s) 12 are accessed by server 10, 110 or 210 (at a fee or free of charge) to obtain desired adverse event data therefrom. In systems 10 and 110, the adverse event database(s) 12 are external to the servers 14 and 114. Hence, servers 14 and 114 desirably store the data received from databases 12 in shadow storage devices 16. Server 214, by contrast, accesses its internal adverse event database(s) 12 for the desired data.

The desired adverse event data having been accessed, the processor 18 of systems 10, 110 and 210 then analyzes the data, as described above, to identify previously known and new essential adverse events, as indicated at step 28. At step 30, the processor 18 further processes the analyzed adverse event data to create useful proprietary essential adverse event information, such as any of the kinds mentioned above. More particularly, in creating the proprietary adverse event information database at step 30, or more preferably an essential adverse event information database, at step 30' (not shown), processor 18 preferably possesses logic whereby it categorizes the newly-discovered essential adverse event(s) associated with a particular product or device that are identified at step 28 and also identifies at least one new use for the product or device responsive to the identification of at least one new essential adverse event(s) associated with the product or device. The processor 18 then stores the essential adverse event information as one or more databases in essential adverse event information storage device 22.

According to presently preferred embodiments of the invention, the data retrieved from adverse event database(s) 12 is processed and analyzed by a centralized processor 18 on server 14, 114 or 214 and the analyzed data is stored at an essential adverse event information storage device also supported by server 14, 114 or 214. Alternatively, the proprietors of servers 14, 114 or 214 license proprietary software to users of user computers 24 that perform the functions of processor 18. Such software is loaded onto the user computers 24 to execute the adverse event data analyzing and other processing functions of processor 18 described above and the generated useful adverse event information may be stored at the user computers 24. In any case, servers 14, 114 and 214 can be directly connected by a user interface 24 such as but not limited to a modem.

It will be understood that the servers 14, 114 and 214 may also be indirectly connected to user computers 24 via one or more other servers, a central computer or other system designed to link computers or other processing machines. Ideally, the information is transferred digitally between servers 14, 114 and 214 and user computers 24. Alternatively, however, it is transmitted in analog form by a modem along standard telephone lines. It is further understood that the information can also be transferred by disk, printed and then scanned in or, alternatively, manually re-keyed.

Preferably, the user computers 24 and their associated printers (not illustrated) are sufficiently sophisticated to organize and print all information generated by the systems 10, 110 and 210 in virtually any desired format and on essentially any desired printable medium that is printed by the printers. However, certain product labels and package inserts that incorporate the information can be manually type faced using typesetting or other conventional printing techniques. The system also formats the data for submission to regulatory agencies such as the FDA.

The proprietary information that is generated by the systems of the present invention is superior in many ways to the limited, and generally static, adverse event data and databases heretofore known in the art. In respect to medical products in particular, the volume of data and the degree to which the data may be stratified and studied, the systems according to the invention far exceed the capabilities of FDA-required pre-marketing studies for medical products. To illustrate, a typical FDA pre-marketing study generally involves study populations of less than about 5000 and normally less than about 2000 participants. In contrast, the adverse event data that is amassed and analyzed pursuant to the invention contains information on far larger numbers of people receiving the medical product. Representative populations studied using the present system in virtually all practical medical product scenarios comprises at least 5000 and is analyzed in any desired increment such as, for example, 5,000; 10,000; 50,000; 100,000; 200,000; 1 million or more.

The systems of the present invention will additionally provide a better appreciation of delayed or latent essential adverse events caused by products or devices long after initiation of treatment or after treatment has been discontinued. Using the present systems, post-exposure follow-up of a product or device is analyzed in any desired increments of time. For instance, selected post-exposure study periods may be as brief as a few minutes or hours to considerably lengthier periods, such as 1 day, 2 days, 7 days, 10 days, 30 days, 90 days, 180 days, 1 year, 3 years, 5 years, 10 years or more.

Risk/benefit analyses may also be readily performed using the methods and systems described herein. Acceptable essential adverse event thresholds may be established and studied for a product or device. The essential adverse event thresholds may be selected to be at any desired incidence level, e.g., 1:10,000,000; 1:1,000,000; 1:100,000; 1:10,000; 1:1,000; 1:100, above which use of a product or device may exceed its benefit for a general or specific population group. The essential adverse event thresholds serve as limits for single or aggregated newly discovered adverse events. For example, an essential adverse event threshold of 1 occurrence in 1000 persons may be established as an acceptable level of occurrences.

If 2 occurrences are observed in the target population then the essential adverse event threshold is exceeded and the product or device is deemed unsafe or commercially impractical for use by persons in that group. Likewise, 10 new similar or dissimilar essential adverse events relating to the product or device may be observed in the target group, but none of the individual new essential adverse events occurs more than once in 10,000 persons. In the aggregate, therefore, the 10 occurrences detected in a total study population of 10,000 persons corresponds to a ratio of 1:1000 which equals, but does not exceed the acceptable essential adverse event threshold for the product or device under scrutiny. In this instance, the product is deemed safe and commercially viable for use in the targeted population group.

The present systems and methods also enable ready comparisons between target populations that receive treatment with a product or device, and experience essential adverse events, with untreated control groups that experience similar essential adverse events. For example, a target group treated with a certain vaccine that acquires diabetes may be compared with an otherwise identical but unvaccinated control group that also acquires diabetes. Increased incidences of diabetes in the target group thus may be attributable to the vaccine.

Systems 10, 110 and 210 may be programmed to establish any desired acceptable increased rates of essential adverse event occurrences in the treated target group versus the untreated control group, e.g., 2%, 5%, 10%, 20%, 30%, 50%, 75%, 100%, 150%, 200%, 300%, 400%, 600%, 800%, 1,000% or more, above which treatment would be contraindicated in the target group. Preferably, the system analyzes data using any desired study design. For example, a case control study design may be used where the frequency of using a product or device in a group with the target disease is compared to the frequency of using a product or device in a group of controls. The studies may include prospective clinical trials and retrospective follow-up of clinical trials, as well as cohort analysis of people not in clinical trials. The studies may, or may not, include efficacy for the intended use as in treatment of a specific disease. The studies may also be part of a pre-approval or post-marketing study regulated by the FDA or similar regulatory body. Conversely, the studies may be unaffiliated with FDA-sanctioned clinical trials.

Returning to FIG. 4, the adverse event information stored in essential adverse event information storage device 22 is commercialized. Commercialization of the useful essential adverse event information may take on an assortment of forms as indicated in FIGS. 5 and 6.

Users of servers 10, 110 and 210 may include individual, a corporation, partnership, government agencies, research institutions or any other persons or entities that may have an interest in or need for new and useful essential adverse event information. Non-limiting examples include manufacturers and/or distributors of products or devices, insurance companies, health maintenance organizations and public health departments. In the case of manufacturers and/or distributors of products or devices, such manufacturers and/or distributors may use the information in the manufacture and/or distribution of their own products, or may license the information to their competitors.

Figure 5:
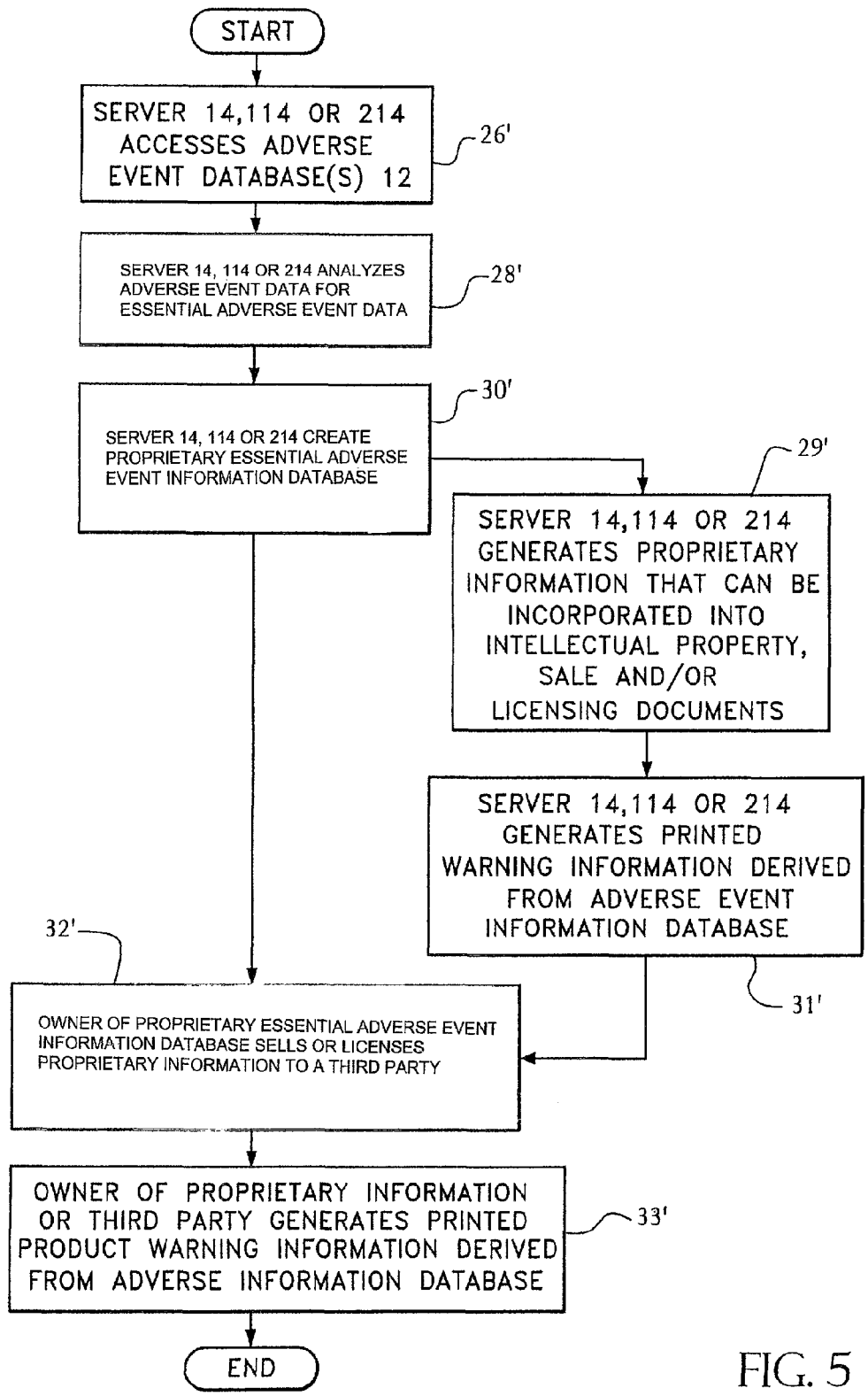
FIG. 5 is a first preferred specific application of the method represented in FIG. 4.
Figure 6:
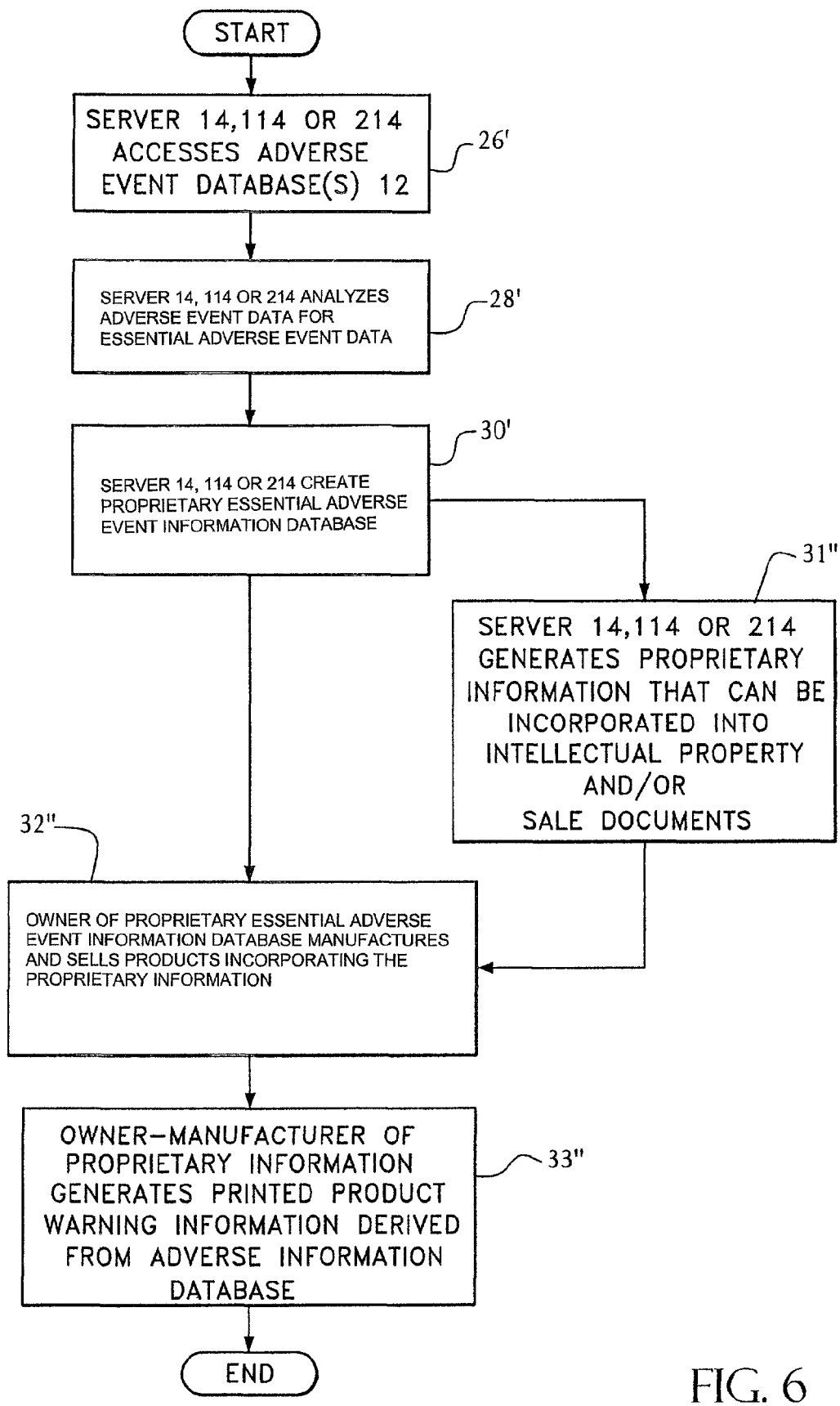
FIG. 6 is a further preferred specific application of the method represented in FIG. 4.

As indicated by step 26' in FIGS. 5 and 6, at the request any of these persons or entities or on its own behalf, the owner or licensee of server, 14, 114 or 214 accesses and retrieves raw adverse event product data from adverse event database(s) 12. At step 28' the server analyzes the retrieved data to identify new essential adverse events regarding a product or device, to conduct cost/benefit analyses related to the newly discovered essential adverse events or to perform any other desired analysis of the raw data. At step 30' the server creates one or more proprietary essential adverse information databases that are stored in essential adverse information storage device 22. At step 32' in FIG. 5 the licensee or owner or owner of server 14, 114 or 214 commercializes the essential adverse event information in essential adverse information storage device 22 by selling or licensing the proprietary information to a third party. The third party communicates with system 10, 110 or 210 through user computer 24. The user computer interfaces with user interface 20 to make requests for information to and to receive information from the processor 18 of server 14, 114 or 214. Interpretation of the received information may be performed by the third party, an independent contractor, the owners or licensees of server 14, 114 or 214 or the owner(s) or licensees of the essential adverse event database(s) 12.

Practical, but non-limiting, examples of possible users of systems 10, 110 or 210 and the method depicted in FIG. 5 include manufacturers and/or distributors of products or devices, holding companies, venture capital companies or other companies or individuals seeking to capitalize on ownership of a portfolio of new product information that may be of commercial value. The users may use the information to seek patent, or other intellectual property protection for the information. The systems 10, 110 and 210 and the methods depicted in FIGS. 5 and 6 are especially useful for creating proprietary information and products or devices. The systems and methods of the present invention can assist in preparing information for a patent application and can assist in documentation of the invention, including inventors, date of invention, progress of the development of invention. As used herein, proprietary information shall be construed to mean information that is used or intended to be used for establishing or claiming specific intellectual property rights. For example, the proprietary information can be used in the creation of intellectual property, sale or licensing documents; that is, the proprietary information may comprise textual or graphical content that may be incorporated into patent applications. A 'proprietary new use' means a new use, in which one has or is seeking intellectual property rights, i.e., a patent.

It is not the intent of this invention to encompass an "expanded use" relating to an unexpected phenomenon associated with a product or device. "Expanded use" is used herein to mean other uses for a product or device in addition to currently known uses for the product or device. For example, if an unexpected phenomenon associated with blood pressure medicine is hair growth, then the use of blood pressure medicine may be expanded to include use as a hair tonic. By comparison, expanded uses for a medical product or device are not created by discovery of adverse events, rather such uses are determined by performing extensive clinical trials and obtaining regulatory approval for marketing the new use of the product or device. On the other hand, the invention is intended to encompass a restricted use, i.e., avoiding, when possible, use of the product or device by methods involving same, or by ups using same, that are at increased risk for an adverse event. A new useful characteristic of a product or device responsive to identifying an essential adverse event, e.g., providing a written warning with the product to a consumer, is also encompassed by the invention. New restricted uses are primarily derived by discovering an adverse event because manufacturers are required to disclose possible adverse events associated with use of a product or device, even if the adverse event has not been proven to occur in a specific risk group or situation. However, the invention is intended to encompass a use that allows a group, previously considered to be at high risk, to use a product by better defining the high risk group, although, this is neither an expanded nor a restricted use.

It is also not the intent of this invention to encompass the simple copyrighting of package inserts that may contain adverse event information. A manufacturer and/or distributor is entitled to the copyright associated with any creative work that it produces, including package inserts. Of course, package inserts may contain adverse event information or product uses that are not proprietary and are in the public domain. This invention is, therefore, not intended to encompass this practice. It is also not the intended purpose of the present invention to encompass proprietary kits (i.e., patented), wherein the kit is proprietary solely because of pre-existing intellectual property rights. Rather, it is the intent of the invention to claim proprietary kits containing new proprietary adverse event information and/or instructions to use the product according to a proprietary new use based on new adverse event information, wherein that new adverse event information is the product of a system, device or method of the present invention.

Users might seek patent protection for new therapeutic uses for existing products or devices based on newly discovered essential adverse event information. Similarly, users might seek protection for new labeling necessitated by the discovery of the new essential adverse event information. For any new use discovered by the systems according to the present invention, the instructions accompanying the product or device for which the new use is identified should desirably warn newly-identified high risk users of the product or device to avoid using the product or device. Likewise, the instructions also inform users who were previously but wrongly identified as high risk users that the product or device may be safely used by them. Preferably, systems 10, 110 and 210 are capable of formatting the proprietary information data such that it is suitable for incorporation into the aforementioned intellectual property documents.

In FIG. 6, method steps 26', 28' and 30' are identical to their counterparts in FIG. 5. However, as indicated at step 32" of FIG. 6, the owner or user of the proprietary essential adverse information commercializes the proprietary information by manufacturing (or causing to be manufactured) products or devices incorporating the proprietary information and then selling the products and devices.

In addition to the functions represented by method steps 26', 28', 30', 32' and 32", additional tasks are preferably performed to more completely fulfil the purposes of the present invention, as reflected in FIGS. 5 and 6. For example, as indicated by step 29' in FIG. 5, server 14, 114 or 214 may be programmed to generate proprietary information, typically in textual and/or graphic form, that is incorporated into intellectual property, sale and/or licensing documents. The documents then are used in negotiations with product or device manufacturers and/or distributors or other interested third parties. Additionally, FIG. 5 reveals in step 31' that server 14, 114 or 214 may optionally generate printed product warning information derived from the essential adverse information database(s). The printed warning information may be used in connection with packaging such as, for example, as product labeling or as product packaging inserts to advise the consumer (or product prescriber in the case of products or devices requiring a prescription) of contraindications or other adverse events associated with use of the product or device. Alternatively, as shown in step 33' of FIG. 5, the owner of the proprietary information or its licensee may generate the aforesaid printed warning information.

Similarly, in FIG. 6, the server 14, 114 or 214 may generate proprietary information that may be incorporated into intellectual property and/or sale documents (step 31"). Printed product warning or safety information is generated by the servers 14,114 or 214. Alternatively, as shown at step 33", this step is performed by the owner or licensee of the proprietary information (who also manufactures and/or distributes the product or device or causes it to be manufactured and/or distributed).

Equipped with the new essential adverse information generated by systems 10, 110 and 210, a user might also urge the FDA to compel existing manufacturers and/or distributors of a product to remove the product from the market if it does not have adequate safety warnings or to prevent those contemplating marketing the product from entering the market without providing adequate safety labeling.

In a preferred application, the systems described herein are used to develop new proprietary safer uses for drugs that are already generic or soon to become generic. A generic drug is one where the active compound either is not protected by a composition of matter patent, or the patent will very soon expire. Therefore the active compound is commercially available and adverse event data may be available from one or more sources. In some instances there are drugs that are on the market but protected by orphan drug status, such as thalidomide or by a use patent such as AZT. In these instances the composition of matter patent had expired but competitors have not entered the market because there are only a few known existing uses for the product, and these are covered by use patents or orphan drug provisions. However, these drugs may have been on the market for ten or more years and little research has been conducted before or during that time to identify and optimize the fullest extent of their potential ranges of safe use. Moreover, they have probably been tested for other indications, and adverse event information exists on them.

In varying degrees, generics of a proprietary drug often differ from the proprietary drug itself, and from one another. More particularly, although their active ingredients may be the same, generic drugs may include impurities, inert substances, carriers and other agents that are not present in their corresponding proprietary drugs or other generic alternatives thereof. When considering generics and their proprietary counterparts based solely on their active ingredients, the generics would be expected to exhibit similar adverse events. However, through implementation of the present invention, generic drugs can be precisely compared against their proprietary drug counterparts, and alternative generics, to determine the impact of their inactive ingredients on adverse events, despite the variability of such inactive ingredients. For instance, drugs with agents which delay the release of an active agent can be expected to exhibit many of the same side effects as drugs with the same active ingredient, but that release it over a shorter period of time. In this context, therefore, a generic and a proprietary drug is considered to be the same product if the adverse event(s) and/or new use(s) for the drugs would be expected to be consistent for both.

The "new use" derived from the new adverse event may involve restricting the use of the product or device in ways that are now discovered to be dangerous. For example, if a product is determined to be flammable or explosive, the "new proprietary use" would restrict its use in conditions that could lead to combustion or explosion, which may occur when used in the presence of an open flame or near a fire. Substances discovered to emit toxic fumes would, as a new use, only be utilized in well-ventilated areas, or under safety hoods. The new use may include providing a kit which contains warnings about a new adverse event relating to use of the product or device.

The term 'commercially available' pertains to products or devices that are available to more than one group or company. The product can be a substance, such as a drug, which is known by more than one company or research group. With such a product or device, adverse event data may have been generated by more than one group, and adverse event data although generated by one group, may not be new. This is because another earlier group may have discovered the adverse event first. This is especially true when the product has been sold commercially, and is known to have been used by a number of different groups over time.

Studies may be performed with non-commercially available products, wherein a non limiting example would be drugs. In this example, the non-commercially available drug may also be tested in patients receiving commercially available drugs. Drug interactions may be detected between the commercially available drug and the non-commercially available drug. In this situation the purpose of the study is to screen a database for adverse events of the non-commercially available product, not the commercially available product. A manufacturer and/or distributor of a commercially available product or device is not required to warn potential users about an interaction that may occur with their product or device and a product or device that is not yet available, or that the manufacturer or distributor does not even know exists. The present invention is intended for screening of products that are both commercially available and those that are not, unless otherwise specified.

Many entities, large and small, may beneficially utilize the systems described herein. A representative, although non-limiting, example would be an independent non-manufacturing company that procures access to one or more essential adverse event databases to analyze the data contained therein and identify new uses for existing drugs. The independent company could then license the "new use" technology or new characteristic it discovers to pharmaceutical manufacturers. The content of the licensing agreements may be agreed upon before or after the data has been analyzed. The independent company may opt to file appropriate intellectual property documents such as patent applications covering the newly-discovered uses for the product and/or their attendant product warning information and receive monies derived from the sale of the drug in the form of royalties or a lump sum fee.

Alternatively, the independent company may utilize the services of a contract manufacturer that will make the drug for the independent company which will reserve the right to sell the product on its own behalf. The independent company may also be a large insurer or pharmaceutical company that has access to its own extensive adverse event information database(s) from which may identify and commercially exploit new uses for existing products or devices.

As mentioned above, the present systems and methods are also utilized to develop proprietary safety information on products or devices unrelated to the medical fields since manufacturers and/or distributors in other fields of endeavor generally are required to provide consumers with safety information regarding their products.

Essential Adverse Event Information

The final determination of what is "essential" information is determined by a regulatory agency such as the FDA.

New adverse event information that is "essential" is of great commercial value since if this information is proprietary, for example patented in the form a new use, it can be used to exclude potential competitors from selling a product which would require the essential information. In order for a company searching through raw adverse new uses, to maximize profits from such a search, the "essential" new uses should ideally be separated from other new uses. By limiting the protection for such new data, e.g., patenting, and limiting petitions to regulatory agencies to only the "essential" new uses, a company saves time and money by avoiding expending time on adverse event information that has little commercial value.

Methods of Determining Essential Adverse Events

A computer system can assist in identifying essential adverse event information. Preferably the first step is to identify adverse events associated with a group or subgroup using or exposed to the product in question.

In accordance with the embodied invention, comparisons are made regarding the risk of the occurrence of a new adverse event in a group of subjects exposed to the product or device, with the occurrence of the same event in a control group. One type of control could be a group exposed to a competing technology (drug, product). For example, if the system is evaluating the use of a fuel, then the control group would be exposed to a competing fuel, such as oil vs. coal vs. natural gas versus electricity. In a like manner, the system could compare those exposed to an oil-based paint versus a latex-based paint as a non-limiting example.

Another type of control group could be a group that receives no exposure to a competing technology. For example, comparing a group receiving a drug, to a group receiving no drug.

A third possible control situation would be a population exposed to the product in question, but selecting a subpopulation, which does not contain people in the same subgroup in which the adverse event is thought to occur more frequently. An example would compare a population receiving 4 doses of a vaccine, to a population receiving only one dose of a vaccine, which is either equal to a bolus of all 4 of the comparable doses, or which is equal to only one of the comparable four doses. Another example would compare a group of people with liver problems, receiving a drug for a non liver ailment, to a group with healthy livers who receive the same drug.

A fourth type of control would use the group members as their own control. In this case the incidence of an essential adverse event occurring prior to exposure to the product or device, is compared to essential adverse events following exposure to the subject product or device.

Having estimated the risk of an adverse event associated with a product, such as a drug, one can determine if the adverse events are essential. Several different criteria can be utilized to determine if the adverse reaction is essential. Such criteria include the non limiting examples, comprising: determining whether the adverse event is unnecessary, if the risk exceeds benefit, if causation has been proven, or if the risk is frequent and or severe. These factors can be determined, and compared or compiled with the assistance of a computer.

An 'unnecessary adverse event' would be an essential adverse event that could be or could have been easily avoided. One example would be a drug interaction, which could be avoided by withholding one of the interacting drugs. Another example of an unnecessary adverse event is one in which the adverse event can be or could have been avoided by using a different product, or even a different brand. For example, if a drug is very toxic in a subgroup of people, e.g., people of a certain age, or those who have a preexisting condition, then the adverse event in such individuals groups can be or could have been easily avoided by using a different drug or different treatment, for example, surgery.

Another type of essential adverse event information is one in which the risk 'exceeds the benefit.' For example, in certain subgroups of patients, the risk of disease or complications exceeds the benefit provided by the product or device.

A third type of essential adverse event information is where the frequency of the adverse event is so high, or the event so severe, that a significant health concern or medical management issue. In a situation the adverse event may occur gradually, but laboratory testing could pick up the damage early, so that further damage need not occur. The frequency of the events that render an adverse event essential depends in part on the severity. Association between death, hospitalization, life threatening events, permanent organ damage, disability, cancer, or birth defect and a product or device, becomes essential adverse event information at a lower frequency than would the information relating to a potentially benign adverse event, such as but not limited to minor pain, swelling, and fever. Other adverse events that are included in this essential category include marked abnormalities in laboratory values, vital signs, EKG, and seizures.

A fourth type of essential adverse event information occurs when the adverse event is so well characterized that causation is generally believed to exist. For example, such a situation can occur when the adverse event is detected in two separate, well-controlled clinical trials, i.e. the adverse events are duplicated. An example would be an industrial chemical, wherein exposure is unintended, but for which exposure is known to cause severe adverse events. By providing warnings, one can alert those who may be exposed of the risks associated with accidental exposure, and the treatment that should be under taken to minimize an adverse event following exposure.

Method of Screening for a Specific Adverse Event, Especially an Essential Adverse Event.

The method of the preferred embodiment can be utilized to develop new methods of screening drugs for adverse events, particularly essential adverse events. The discovery of an essential adverse event warrants that all manufacturers and/or distributors of the product or generic version to warn of the adverse event. In certain circumstances where a competitor produces a similar or even identical (generic) the competitor may be given the choice of warning potential consumers of the adverse event, or of performing a study to disprove-the product is related to or causes the adverse event, or disprove the that adverse event is essential. In the later case this embodiment pertains to specific tests to insure a product is safe, which comprises specifically checking to see if the product is associated with or causes the adverse event which is also associated with the competing product.

A competitor can perform specific tests to try to disprove the existence of an essential adverse event. This can be of value to a competitor when an adverse event information is covered in a patent (i.e., proprietary adverse event), and inclusion of this adverse event in a product data safety sheet (for example pharmaceutical labeling/package insert or an advertisement) or an instruction brochure, pamphlet or book for a device, would constitute an act of infringement. Alternatively, a competitor can perform a study to either try to disprove the existence of an adverse event or try to disprove that the adverse event is 'essential.' In the later case the competitor may use the same or different data as was used in establishing the adverse event in the first place, or that established that the adverse event is essential. The competitor can also use the same or different epidemiological method, and the same or different statistical tests. Moreover, the competitor can provide additional data to supplement the initial data, such as information regarding confounding variables that may be useful for disproving the essential adverse event information. Computers can assist in this process as provided above.

By avoiding the placement of proprietary adverse event information in a product data safety sheet or the like, a competitor avoids infringement of patents. This is because what was claimed as an essential element in the patent or what appeared to be inherent in the claimed invention, is no longer required in the competitors product. Such an improvement will avoid costly patent litigation and lead to lower costs of development of a product or device, quicker time from development to market, or an expected higher return for development costs.

Nevertheless, the present invention is not intended to encompass pharmacogenomic techniques for screening.

Licensing Agreements.

The invention provides new methods of business that provide to a manufacturer and/or distributor the ability to prevent a third-party, potential competitor from generating proprietary 'essential' information with regard to the manufactured or distributed product or device, thereby preventing the manufacturer's and/or distributor's exclusion from the market. A preferred embodiment of this method involves using a licensing agreement/contract for sales of the product or device, which states that the product or device can only be used for certain purposes. Such a license would exclude the licensee's right to the use the product or device to determine new proprietary characteristics or uses for the subject product or device, for the situation in which the new characteristic or use is discovered by screening for the occurrences of new adverse events related to the use of the product or device.

The license or agreement could be similar to that used with software (e.g., a shrink-wrap license), where the breaking of the wrapper or of a seal indicates one's acceptance of the contract. Such a licensing agreement could be affixed to or accompany the product or device, by methods well known in the art. Alternatively, it could be signed by a responsible party prior to delivery of the product or device to a purchaser, end-user, distributor, etc. Moreover, as part of the contract/licensing agreement, the purchaser, end-user, distributor, or the like, would agree for a predetermined period of time not to use the product or device in any attempt to discredit the existence of one or more new, essential adverse events, or the utility of the existing subject proprietary use.

This will prevent competitor licensees from trying to block the original owner's rights to the product or device by 'discovering' through the use of essential adverse event information, proprietary new characteristics or uses of the product or device. For example, if the competitor were to find or become aware of a previously unknown, essential adverse event, and if that information were proprietary to the competitor, such a competitor could have a basis for claiming exclusive rights to a novel product or device, which would be just like the original, except it claims a new characteristic based upon the newly discovered essential adverse event information. However, the agreement controlling rights to use the product or device would preclude such behavior.

Alternatively, or in addition to an end-user agreement, a licensing agreement can be made at the time of intermediate sales of products or devices to wholesalers, retailers, distributors or other who purchase the product or device with the intent of reselling it to third parties. Such an agreement can be in the form of, or include, an electronic monitoring system. In one such embodied electronic system, a window would appear or a button would require activation, acknowledging acceptance of, and intent to comply with, the contract/licensing agreement. In an alternative embodiment, an electronic signature, acknowledging acceptance of and compliance with the agreement would be stored. In a third possible electronic method, an electronic image of an 'executed' agreement document would be saved.

A manual packaging system can also be established which could be utilized in shipments to purchasers of large quantities of the product or device, such as but not limited to wholesalers, retailers, middleman, merchandisers, distributors and the like. A seal could be applied to the bulk package, that when broken, would certify agreement with a licensing agreement of the type(s) described above.

Based upon this disclosure, one skilled in the art can devise any of a number of different methods or systems to accomplish the task of creating and/or verifying an agreement, electronically or otherwise, that would prevent the purchaser and/or the end-user from using the product or device in certain ways or for certain purposes, specifically for generating proprietary new, essential adverse event information to be used for the identification and/or development of new characteristics or uses of the subject product or device, and/or new methods of screening such products or devices for such new, essential adverse event information.

Methods of Screening Adverse Events for Commercial Value.

All essential adverse event information is not of equal value. Value depends on the potential value of making a generic product or device into a proprietary product or device, or preventing a proprietary product or device from becoming a generic product or device. If a proprietary product or device is loosing money or marginally profitable, then extending its proprietary status by discovering essential adverse events will add little value. For example, discovering an essential adverse event in a generic aluminum-containing antacid may not bring much added profit, even if the product were to become proprietary, if consumers were more interested in switching to other antacids lacking aluminum, such as calcium-based antacids or magnesium-based antacids. Alternatively, a consumer with gastritis who is faced with the proposition of buying expensive antacids, may prefer to use alternative newer, more expensive, and more effective products, such as histamine blockers or hydrogen pump inhibitors. Alternatively, large profits can be made on a highly profitable patented product or device by extending its proprietary status by obtaining one or more new patents based upon the discovery of essential adverse events associated with use of the product or device.

In a preferred embodiment of the invention, a product or device for which an essential adverse event is discovered, is also one that is highly profitable, but would face a marked decrease in profitability if the product or device were to lose its proprietary status. One skilled in the art can screen products or devices by recognized methods to determine the potential value of discovering proprietary essential adverse events. Those skilled in e.g., sales, marketing, licensing, statistics or business practices, will know how to use recognized methods to calculate or estimate such parameters as, in the non limiting examples of, current market share, potential market share, total market share in unit volume or sales, marketing costs, elasticity of demand, cost of production, cost of marketing, number of competitors, market potential, cost of discovering a new adverse event, product liability costs, growth of market and the like. Mathematical modeling, with or without the use of computers, can be performed to evaluate whether it would be profitable to develop a proprietary essential new use based on an essential new adverse event. In addition to profitability, an entity may desire to determine cost of capital and opportunity costs before deciding to move forward with the project.

All references cited herein, including journal articles or abstracts, U.S. or foreign patents, published patent applications, or any other references, are entirely incorporated by reference herein, including all data, tables, figures, and text presented in the cited references. Additionally, the entire contents of the references cited within the references cited herein are also entirely incorporated by reference.

It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art. Reference to known method steps, conventional methods steps, known methods or conventional methods is not in any way an admission that any aspect, description or embodiment of the present invention is disclosed, taught or suggested in the relevant art.

While the foregoing specification has been described with regard to certain preferred embodiments, and many details have been set forth for the purpose of illustration, it will be apparent to those skilled in the art that the invention may be subject to various modifications and additional embodiments, and that certain of the details described herein can be varied considerably without departing from the spirit and scope of the invention. Such modifications, equivalent variations and additional embodiments are also intended to fall within the scope of the appended claims.

What is claimed is:

1. A method of commercializing at least one previously unreported proprietary method of using a product of manufacture or device, wherein the proprietary method of using the product or device is established according to the steps comprising:

accessing one or more data sources, wherein at least one data source stores adverse event data associated with the product or device;

analyzing and comparing the stored adverse event data, with at least one previously-known adverse event associated with the product or device;

identifying at least one previously unreported essential adverse event associated with the product or device from the adverse event data, wherein an essential adverse event is one regulated by a regulatory agency requiring disclosure of the event in a package insert or data sheet accompanying the product or device, and wherein an essential adverse event is unreported if it has not been reported in any known accessible database, and then responsive to identifying of the previously unreported essential adverse event, identifying at least one previously unreported method of use for the product or device associated with said identified essential adverse event;

documenting inventorship of the at least one previously unreported method of use for the product or device; and creating a database of proprietary essential adverse event information, wherein the database comprises at least one of: a patent, patent application, patent publication, or data contained in at least one patent, patent application or patent publication, said at least one patent, patent application, patent publication, or data contained in at least one patent, patent application or patent publication, which discloses and relates to at least one of the at least one previously unreported method of use and the at least one essential adverse event, and wherein the at least one previously unreported proprietary method of using a product or device consists of a use selected from the group consisting of a restricted use of said product or device, providing warning(s) about the essential adverse event, providing instruction(s) for avoiding an essential adverse event, and any combination thereof; and commercializing the at least one previously unreported proprietary method of using a product or device, the commercializing comprising exclusively disclosing the at least one previously unreported proprietary method of use and the associated at least one previously unreported essential adverse event information, which information, once identified, must then accompany the product or device.

2. The method of claim 1, wherein said computer system generates proprietary information that is incorporated into intellectual property, sale and/or licensing documents.

3. The method of claim 1, wherein said computer system generates printed product warning information derived from the essential adverse information database(s).

4. The method of claim 3, wherein said computer system generates the printed warning information in connection with packaging such as, for example, as product labeling or as product packaging inserts to advise the consumer (or product prescriber in the case of products or devices requiring a prescription) of contraindications or other adverse events.

5. The method of claim 1, further comprises determining value of commercializing the at least one use determined from the at least one identified essential adverse event, wherein the value depends on a potential value of making a generic product or device into a proprietary product or device, or preventing a proprietary product or device from becoming a generic product or device.

6. The method of claim 5, wherein the product is commercially available at the time of the analyzing step.

7. The method of claim 5, wherein the step of commercializing further comprises formatting the data relating to at least one adverse event associated with exposure to, or use of the product or device, or documenting same, such that a manufacturer or distributor of the product or device must inform consumers, users or individuals responsible for the user, physicians or prescribers about at least one adverse event associated with exposure to or use of the product or device.

8. The method of claim 1, wherein the product or device is commercially available at the time of the analyzing step, and wherein the at least one data source comprises information relating to patents and patent applications.

9. The method of claim 1, wherein the product or device is commercially available at the time of the analyzing step, and wherein the at least one data source comprises information relating to raw commercial or sales data, wherein said raw data is commercial or sales data before being processed and analyzed.

10. The method of claim 5, wherein the at least one adverse event comprises a drug interaction.

11. The method of claim 10, wherein the at least one data source comprises information relating to raw commercial or sales data, wherein said raw data is commercial or sales data before being processed and analyzed.

12. A proprietary kit containing a product or device, and labeling notifying a user of at least one previously unreported essential adverse event for the product or device, wherein the kit is used in accordance with the method of claim 1.

* * * * *